United States Patent [19]

Primbsch

[11] 4,275,963
[45] Jun. 30, 1981

[54] METHOD AND APPARATUS FOR SENSING ULTRASONIC ENERGY

[75] Inventor: Erik Primbsch, Cologne, Fed. Rep. of Germany

[73] Assignee: Krautkramer-Branson, Inc., Stratford, Conn.

[21] Appl. No.: 123,377

[22] Filed: Feb. 21, 1980

[30] Foreign Application Priority Data

May 8, 1979 [DE] Fed. Rep. of Germany ....... 2918384

[51] Int. Cl.³ .......................... G01B 11/16; G01B 9/02
[52] U.S. Cl. .................................. 356/35.5; 356/319; 356/360
[58] Field of Search ......... 356/32, 35.5, 352, 358–360, 356/371, 311, 319, 446; 73/655–657, 659, 800

[56] References Cited

U.S. PATENT DOCUMENTS

| | | | |
|---|---|---|---|
| 3,145,252 | 8/1964 | Herriott | 356/359 |
| 3,804,521 | 4/1974 | Sprague | 356/359 |
| 4,046,477 | 9/1977 | Kaule | 356/35.5 |
| 4,145,140 | 3/1979 | Fujii | 356/371 |
| 4,180,324 | 12/1979 | Primbsch | 356/35.5 |

OTHER PUBLICATIONS

Abdulladir et al. "Optical Surface Roughness & Slopes Measurements with a Double Beam Spectrophotometer", Rev. Sci. Instrum. 11-1974, pp. 1356-1360.

Primary Examiner—John K. Corbin
Assistant Examiner—Wm. H. Punter
Attorney, Agent, or Firm—Ervin B. Steinberg; Philip J. Feig

[57] ABSTRACT

The acoustic energy responsive deformation of a workpiece surface is sensed in a contact-free manner by optical means using a laser which illuminates the surface at which deformation is expected. The reflection light energy is transmitted to an optical interferometer as previously shown in the art. The present improvement comprises the use of a multi-wavelength laser beam light and separating the light after passing through the interferometer into the distinct wavelengths. Each light signal corresponding to a specific wavelength is converted individually to an electrical signal, each electrical signal is rectified, and the plurality of rectified signals are then averaged in an electrical summing means.

5 Claims, 1 Drawing Figure

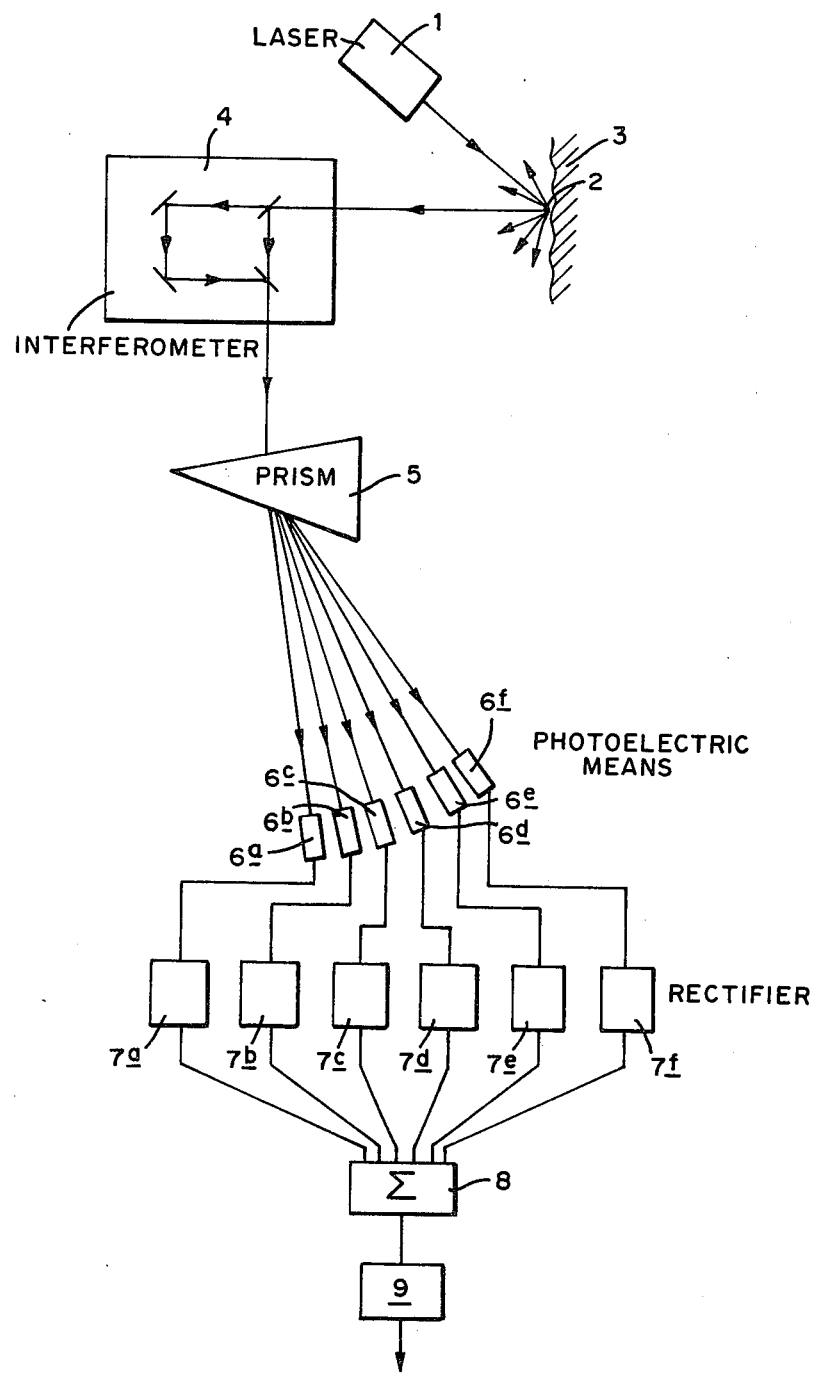

METHOD AND APPARATUS FOR SENSING ULTRASONIC ENERGY

BRIEF SUMMARY OF THE INVENTION

This invention concerns a method and apparatus for sensing ultrasonic energy when testing a workpiece by the nondestructive test method. More particularly, this invention concerns a method and apparatus for sensing by optical means the ultrasonic energy responsive surface deformation on a workpiece using laser beam energy and an optical interferometer means wherein the optical signals from the interferometer are transformed to electrical signals, and such signals, in turn, are used for evaluation of the workpiece.

When sensing ultrasonic energy propagated in a workpiece by interferometric means, for instance as shown in U.S. Pat. No. 4,046,477 issued to Walter Kaule on Sept. 6, 1977, the surface of the workpiece is illuminated by monochromatic laser light. The surface deformation caused by the propagation of the ultrasonic energy and occurring at the frequency of the ultrasonic energy causes a phase modulation of the reflected light and the interferometer transforms the phase modulation to an electrical signal whose amplitude is proportional, for instance, to the displacement amplitude of the acoustically excited workpiece surface. A disadvantage of such interferometric arrangements resides in the fact that a mechanical change of the length, such as changes in the interferometer, results in a shift of the working point for transforming the phase modulation into an electrical signal of a given amplitude. This shift, in turn, reflects itself as a time responsive change of the sensitivity of the sensing means for the ultrasonic energy. Length changes or shifts of critical optical parts in the interferometer can occur as the result of thermal expansion or vibration, for instance ambient sound. A further disadvantage of the prior method concerns the rough workpiece surface which is generally encountered on actual workpieces. Such a surface causes a statistic brightness distribution as a result of the uneven light diffraction of the viewed area. This effect is known as granulation. In response to the relative motion of the workpiece surface when sensing such motion by interference means, the granulation texture of the illuminated workpiece portion undergoes motion which manifests itself as additional, but interfering, amplitude modulation. Such modulation is superposed upon the signal used for evaluating the workpiece and, hence, causes a degradation of the latter signal. Therefore, the sensitivity of the signal indicative of the ultrasonic wave energy is reduced.

The purpose of the present invention is the provision of a method and apparatus for reducing the unavoidable working point shifts and the interfering modulation resulting from granulation to such an extent that the evaluation signal is no longer adversely affected.

The problem existing heretofore is solved by the following sequence of steps:

the workpiece surface is illuminated with a beam of laser light which contains two or more discrete wavelengths;

the reflected light derived from the workpiece surface is passed through an optical interferometer means;

the reflected light after passing through the interferometer means is separated into its original discrete wavelengths;

each of the discrete monochromatic light beams is passed to separate photoelectric sensing means;

the electrical signals produced by the sensing means are rectified in individual rectifiers, and the rectified signals are addititively summed to provide a summation signal which contains information responsive to the deformation dependent motion of the workpiece surface.

DESCRIPTION OF THE DRAWINGS

The single FIGURE is a schematic illustration of the present invention.

DETAILED DESCRIPTION OF THE INVENTION

An argon laser 1 illuminates a surface portion 2 of a workpiece 3 with six discrete wavelengths of light. A portion of the light reflected at the workpiece surface is passed through an optical interferometer 4 as shown for instance in U.S. Pat. No. 4,046,477 supra, and thereafter is split, preferably by optical means, such as a prism 5, into six wavelengths, each wavelength being responsive to a different angle of refraction. Each of the diverging light beams is incident upon a respective photoelectric means 6a through 6f so that each photoelectric means receives one of the light wavelengths. Rectifiers 7a through 7f are coupled in series with the respective photoelectric means. The six rectified electrical signals obtained from the rectifier are then additively mixed by a summing means 8 to produce the required averaged output signal. If desired, the output signal can be fed to an isolation stage 9 from where the signal can be used for evaluation, that is, deriving information responsive to the ultrasonic energy dependent motion of the surface portion 2 as sensed by optical means free of physical contact. The amplitude of the electrical signal, depending upon the working mode of the interferometer, is proportional to, or otherwise mathematically a function of, the amplitude of the acoustic energy responsive surface deformation of the workpiece area illuminated by the laser beam.

The invention is based upon the thought that when several monochromatic wavelengths of laser light are used and the wavelengths are divided into several receiving channels, the point of operation in the optical receiving means, for example interferometer, and the occurring granulation are dependent upon the wavelength of the light. Hence, for each discrete wavelength there is a different working point and different receiving conditions which are subject to temporal changes or variations. For instance, responsive to dimensional shifts of optically active parts within the interferometer resulting from thermal or other causes and/or other illumination changes due to granulation, there can occur at the output of the interferometer for each discrete wavelength a condition which causes the interference beams (reference beam and measuring beam) to become cancelled or severely attenuated. This would cause a collapse of the acoustic energy dependent output signal. However, such an unfavorable condition will hardly occur coincidently with another discrete laser light wavelength which preferably remains equidistantly spaced. Hence, the probability of a usable output signal being present is greatly enhanced, particularly if the several signals are summed after electric signal rectification. In practice, several discrete wavelengths of the laser beam light are available, six as illustrated in the present example, so that adequate assurance is provided for sensing the ultrasonic energy by optical means substantially without disturbance.

What is claimed is:

1. Method for sensing by optical means the surface deformation of a workpiece resulting from ultrasonic energy which is propagated in such workpiece comprising:

illuminating the workpiece surface where such deformation is to be sensed with a laser beam whose light spectrum contains a plurality of discrete wavelengths;

passing the laser beam light reflected at the workpiece surface through interferometer means;

separating the laser beam light from the interferometer means into separate light beams corresponding to said plurality of discrete wavelengths;

providing a plurality of electrical signals corresponding to said light wavelengths;

rectifying separately each of said electrical signals whereby to provide a plurality of direct current electrical signals, each signal responsive to the intensity of light of a respective wavelength, and summing said direct current electrical signals.

2. The method for sensing as set forth in claim 1, said separating said laser beam light into separate light beams comprising passing said light beam through an optical prism.

3. Apparatus for sensing by optical means the surface deformation of a workpiece resulting from ultrasonic energy which is propagated in the workpiece, comprising:

a source of laser beam light having a plurality of discrete wavelengths disposed for illuminating a surface portion of a workpiece where acoustic energy responsive deformation is to be sensed;

an optical interferometer means disposed for receiving the light reflected at said surface portion and for providing a measuring light beam portion and reference light beam portion which are brought to interference;

light beam separating means disposed for receiving said light from said interference means and producing a plurality of substantially monochromatic light beams corresponding to said discrete wavelengths;

a plurality of photoelectric sensing means, one for each of said wavelengths, disposed for receiving each such light beam and providing a corresponding electrical signal;

rectifying means coupled to said photoelectric sensing means for rectifying separately each of said electrical signals, and summing means coupled for receiving said electrical signals to provide a time responsive averaged signal of said electrical signals.

4. An apparatus for sensing as set forth in claim 3, a signal isolation means coupled for receiving said averaged signal from said summing means.

5. An apparatus for sensing as set forth in claim 3, said light beam separating means comprising an optical prism.

* * * * *